United States Patent [19]

Gulyás et al.

[11] Patent Number: 4,753,928

[45] Date of Patent: Jun. 28, 1988

[54] PROCESS FOR OBTAINING SEXUAL PRODUCTS FROM MAMMALS SUITABLE FOR NATURAL OR ARTIFICIAL FERTILIZATION

[75] Inventors: Tamás Gulyás; Csaba Bánházi, both of Szekszárd; Zoltan Graf, Budapest; Anikó Horváth, Budapest; György Kéri, Budapest; Eszter Kováts, Budapest; István Teplán, Budapest, all of Hungary

[73] Assignee: INNOFINANCE Altalanos Innovacios Pengintezet, Budapest, Hungary

[21] Appl. No.: 886,618

[22] Filed: Jul. 18, 1986

[30] Foreign Application Priority Data

Jul. 18, 1985 [HU] Hungary ............... 2251/2763/85

[51] Int. Cl.$^4$ .................................. A61K 37/43
[52] U.S. Cl. .................................. 514/15; 514/800
[58] Field of Search .................................. 514/800, 15

[56] References Cited

U.S. PATENT DOCUMENTS

| | | | |
|---|---|---|---|
| 3,836,640 | 9/1974 | Laurence | 514/800 |
| 3,853,834 | 12/1974 | Shields | 514/800 |
| 3,853,837 | 12/1974 | Fujino et al. | 514/800 |
| 3,914,412 | 10/1975 | Gendrich et al. | 514/800 |
| 3,917,825 | 11/1975 | Matsuzawa et al. | 514/800 |
| 4,072,668 | 2/1978 | Amoss et al. | 514/800 |
| 4,075,191 | 2/1978 | Beddell et al. | 514/800 |
| 4,211,769 | 7/1980 | Okada et al. | 514/800 |
| 4,218,439 | 8/1980 | Rivier et al. | 514/800 |
| 4,244,946 | 1/1981 | Rivier et al. | 514/800 |
| 4,255,420 | 3/1981 | Bergfeld et al. | 514/800 |
| 4,256,737 | 3/1981 | Nestor et al. | 514/800 |
| 4,261,887 | 4/1981 | Amoss et al. | 514/800 |
| 4,647,552 | 3/1987 | Gulyas et al. | 514/800 |
| 4,673,665 | 6/1987 | Humke | 514/800 |

*Primary Examiner*—Delbert R. Phillips
*Attorney, Agent, or Firm*—Keil & Weinkauf

[57] ABSTRACT

The invention relates to a process for producing sexual products suitable for natural or artificial fertilization from mammalia through controlling the activity of their sexual organs in their pre- and post-natal lives, during their infancy, puberty and mature state and, in a given case, to produce offsprings from them as well as to increase several times the production of sexual products to a level far above that typical of the life's performance of the species. According to the invention the mammalia are treated at least once and at most 60 times with a compound of general formula (I), $$\text{Glp-His-Trp-Ser-Tyr-}X_1\text{-}X_2\text{-}X_3\text{-Pro-}X_4, \qquad (I)$$

wherein $X_1$ means a glycil-group or any other natural or synthetic D-aminoacid group, $X_2$ means an L-aminoacid-group with a side chain of an alkyl-, phenyl, or triptophyl group containing 1-4 carbon atoms, $X_3$ means an L-aminoacid group having a side chain of an alkyl group with 1-4 carbon atoms or an alkanoyl-amide group of 2-4 carbon atoms and $X_4$ means a glycil-amide or an alkylamide group of 1-4 carbon atoms, or a salt or metal complex thereof in a dose of 0.01 to 500 µg/body weight kg (bwkg), preferably 1 to 100 µg/bwkg, wherein intervals of at least two hours and at most 7 days, preferably 2 to 8 hours, are kept between the individual treatments.

9 Claims, No Drawings

PROCESS FOR OBTAINING SEXUAL PRODUCTS FROM MAMMALS SUITABLE FOR NATURAL OR ARTIFICIAL FERTILIZATION

The invention relates to a process for producing sexual products suitable for natural and artificial fertilization from mammals through controlling the activity of their sexual organs in their pre- and post-natal lives, during their infancy, puberty and mature state and, in a given case, to produce offsprings from them as well as to increase several times the productin of sexual products to a level far above that typical of the life's performance of the species.

The use of various hormonal products, such as steroids, gonadotropins, and more recently GnRH and its certain superactive analogues, is becoming more commonly used in order to stimulate sexual activity and to induce ovulation mainly in domestic animals and those kept for breeding. Substances and also processes known today induce ovulation only in already ripened ovum which has not been able to ovulate for some reason. They are capable of removing some obstacles occurring in the course of normal cycle through a hormonal effect in a single, impulse like fashion and thus induce ovulation. At present no hormonal preparation or process is known which stimulates the action of the ovary in general and stimulates the ripening of preantral and primordial follicles, or one that increases the number of follicles that have started to develop.

At present there is also no known preparation or process which enables the production of ready for fertilization sexual products from immature animals or from animals whose said products have ceased to mature at an early stage, or from intact animals in vitro, or from gonads post mortem.

In the case of several bred animals it is the unsuitable keeping, whereas with certain exotic, wild and furry animals it is the unnatural keeping that causes a regression and sometimes a complete stop in their production of sexual products. In the case of these animals hormone preparations known to date have been generally ineffective.

Recently, with the introduction of species-specific GnRH derivatives [J. A. King and R. P. Millar, J. Biol. Chem. 257, 10722-28 (1982); N. Sherwood et al., Proc. Natl. Acad. Sci. 80, 2794-2798 (1983)] and the fact that technical literature speaks of the presence of various GnRH factors in the gonads and the ovary [R. M. Sharpe et al., Nature 290, 785-787 (1981); N. Dekel et. al., Biol. Reprod. 28, 161-166 (1983)], the idea of special governing factors existing and the possibility of interaction between them has been raised.

Fish- and bird-specific GnRH derivatives worked out by us are suitable to produce sexual products even in the case of fish that would not normally breed in captivity, as described in published Hungarian patent application No. 4457/83. This effect is achieved through stimulating follicle growth.

Aim of the invention is to work out a process whereby one can stimulate the activity of the sexual organs in mammalian offsprings or animals in such a way that their sexual products produced are suitable for artificial or natural fertilization, and for the production of offsprings. Further aim of the invention is to increase the production of sexual products in the male and female organs of mammalia far above the level which is typical in the life's performance of the species.

The invention is based on the recognition that by using compounds of the general formula (I)

$$\text{Glp-His-Trp-Ser-Tyr-}X_1\text{-}X_2\text{-}X_3\text{-Pro-}X_4, \qquad (I)$$

wherein
- $X_1$ means a glycil-group or any other natural or synthetic D-Aminoacid group,
- $X_2$ means an L-aminoacid-group with a side chain of an alkyl-, phenyl, or triptophyl group containing 1-4 carbon atoms,
- $X_3$ means an L-aminoacid group having a side chain of an alkyl group with 1-4 carbon atoms or an alkanoyl-amide group of 2-4 carbon atoms and
- $X_4$ means a glycil-amide or an alkylamide group of 1-4 carbon atoms, or a salt or metel complex thereof the above-mentioned aim can be achieved, that is ready for fertilization sexual products suitable for natural or artificial fertilization can be produced and their volume can be increased in vivo from mammalia that are not sexually mature or are in an unoestrous condition, or their unoestrous condition is due to unnatural keeping, or in vitro from intact animals as well as from sexual organs of mammalia post mortem.

The production of compounds of the general formula (I) is known from the published Hungarian patent application No. 4458/1983 and U.S. Pat. No. 4,410,514.

Based on the above, the invention relates to a process for producing sexual products suitable for natural or artificial fertilization from mammalia (hereinafter: media) through controlling the activity of their sexual organs in their pre- and post-natal lives, during their infancy, puberty and mature state and, in a given case, to produce offsprings from them as well as to increase several times the production of sexual products to a level far above that typical of the life's performance of the species. According to the invention the media are treated at least once and at most 60 times, preferably 1-5 times, with a nonapeptide-alkylamide or a decapeptide-amide of the general formula (I) or a salt or metal complex thereof in a dose of 0.01 to 500 μg/body weight kg (bwkg), preferably 1 to 100 μg/bwkg, wherein intervals of at least two hours and at most 7 days, preferably 2 to 8 hours, are kept between the individual treatments.

The compounds of general formula (I) can be used favourably as solutions, powders, injections or sprays. The way of administering can be intramuscular, intraperitoneal, subcutaneous, intrauterinal etc.

In the case of certain animal species, the production of sexual products increases as a result of the process according to the invention, in the case of other animals (clinical cases) decreased or discontinued sexual activity becomes normal and reaches a level typical of the species. The process according to invention is suitable to induce hyper-production in the sexual organs and thus to increase the volume of the sexual products to a level far above that typical of the life's performance of the species.

In the process according to the invention, by forcing the germinal epithelium into increased activity, the number of motile sperms in the ejaculate is increased.

The process according to the invention gives an opportunity to bring about a hypophysis-hyperproduction, which results in insensitivity of the hypophysis, that is an impassive state of hypophysis develops, thus the process can also be used for contraception.

With the process according to the invention the end-products can be produced under natural and artificial as well as laboratory conditions.

By administering the GnRH analogues of general formula (I) in different rhythms the controlled and above-described functioning of the sexual organs can be achieved which is a yet unpublished, new phenomenon.

The main advantages of the process according to the invention are as follows:

(a) Using the process, gonad activity of mammalia kept under unnatural conditions can be improved, its functioning can be returned to normal, thus the animals become capable of producing offsprings.

(b) The process is suitable to induce hyperproduction in the ovary which makes it possible to increase the number of ovulating ova beyond that which is typical of the species. These, in turn, after in vitro fertilization, can be saved as embryos or can be carried out by recipient animals naturally.

(c) The process is suitable to induce hyper-stimulation and thus super-ovulation in infant individuals of mammalia. Thus one can obtain offsprings from a medium even then when it is sexually immature.

(d) The process is suitable under unique laboratory conditions to produce in vitro fertilizable ova in organ cultures, from intact ovary. Thus, even after the death of the medium, offsprings can be had from animals of high breeding value.

(e) By distributing sexual products obtained through the process, hybridization between species separated by continents becomes a possibility and thus new domestic animal species can be produced.

(f) The process is suitable to produce large numbers of ova, sperms or embryos amongst male and female mammalia of any age group, under industrial type production conditions, and this enables the formation of embryo banks, for example, and the intercontinental distribution of the offsprings.

(g) The process is suitable to relieve seasonal unoestrus and hindered spermatogenesis in mammalia. This way live offsprings can be produced in any season, whereby a better utilization of farming establishments is made possible.

(h) The process is suitable for the artificial breeding of protected rarities of nature.

(i) The process is suitable to render the hypophysis insensitive equally in male and female animals, thus unwanted pregnancies can be avoided even in those instances when known contraceptives cannot be used.

The process according to the invention is further illustrated by the following non-limiting Examples.

EXAMPLE 1

Super-ovulation induced in infant female rats 60 pieces of 21-day old infant rats weighing 7–8 g were treated with D-Phe$^6$-Gln$^8$-GnRH in normal saline solution intraperitoneally. The animals, depending on the treatment they were having, were placed into different groups. In the series of treatments lasting 1–8 days, 1 and 2 μg doses, respectively, were administered daily and twice daily. Treatments were finished with 5 and 10 μg doses, respectively.

After treatment all animals were killed with vapour of ether and their ovaries were removed after the animals died and 24 hours after the last treatment. Evaluation was done visually and from hystological samples. We found several developing follicles in the ovaries of the control animals, but not one of them was of Graf-follicle size, and neither corpur luteum, nor corpus haemorrhagicum could be detected. On the other hand, in all treated groups hormonal effect could be seen which made itself evident by the growing of follicles, by their turning into Graf-follicles, by their ovulation and the forming of regular corpus luteum. Enlarging of the oviduct and the uterus was also evident. Only 4 animals out of 60 did not react to the treatment. In the group that received for 4 days 2 μg of GnRH analogue twice daily and on the 4th day the 2 μg treatment was followed by a 10 μg dose, in the ovary of all animals immediately before ovulation softened Graf follicles could be observed in large numbers. Graf-follicles passing final maturity numbered between 60 and 90, whereas in mature animals this number reached only 12. The same method of treatment was used with the other group of animals with the difference that treatment lasted six days. In this group super-ovulation was judged by the number of regular corpora lutea. In this group, similar to that described above in detail, the number of the corpora lutea varied between 60 and 90 amongst the animals. Hystological evaluation gave full support to the results reached here.

With the process described in detail above, we have been able to achieve, firstly, that mature ova be produced by infant animals and, secondly, that the number of ova produced increased, compared to the value found with adult animals.

EXAMPLE 2

Inducing super-ovulation in infant female mice

With the method described in Example 1, altogether 105 female 28-day, old mice of 5–6 g were treated. The animals treated for 1–8 days were administered 1–5 μg D-Phe$^6$, Gln$^8$, des Gly$^{10}$-GnRH twice daily. 4 hours interval was kept between treatments. Ovaries were removed 27 hours after the last treatment.

Ovaries of the control group had a dull yellow colour, homogen structure and in some of the ovaries 1–2 growing follicles could be observed. In the ovaries of all treated animals enlarged ovaries and oviducts showed the effect of a hormone. The animals received a 1 μg daily dose for three days, then on the third day, 4 hours after the 1 μg dose, 5 μg of the above GnRH was administered to them. In their ovaries there were Graf-follicles past final maturity and of wavy structure, numbering 45–70 in each animal. In a similar group treated for 5 days, in place of Graf-follicles of the quoted number, corpora lutea were formed. Hystological evaluation produced similar results to those of the visual evaluation.

Results of this test gave support to the process described in Example 1.

EXAMPLE 3

Inducting super-ovulation in infant domestic rabbits 20 42-day old rabbit whelps of the white pearl variety reared under large scale farming conditions were administered twice daily for three days 5 μg of D-Phe$^6$, Gln$^8$-GnRH analogue intraperitoneally. Then the animals were divided into two groups and the one half of them was treated with 50 μg of active ingredient on the 4th day while the other half was killed with vapour of ether before treatment began. Developed follicles of this group were counted and used as control in determining the effect of the 50 μg dose. From the group kept alive, two animals were selected and through laparoscope probing their ovulation process was monitored for 10 hours while the animals were kept under narcosis (abdominal cavity was mirrored). The treatment using 50 μg dose after 26 hours resulted in 30-40 ovulations and corpora haemorrhagica, respectively, in each of the animals as opposed to the inactive ovaries of the control animals.

With this process in infant rabbits already ripened ova have been produced and their number was successfully increased compared to the physiological value.

EXAMPLE 4

Inducing super-ovulation in infant pigs 20 100-day old infant female pigs were treated for 6 days, twice daily, with 10 μg doses each consisting of D-Phe$^6$-Gln$^8$-GnRH analogue administered intramuscularly. In the test half side of the ovaries in the control animals was removed and, by using the test method detailed in Example 3, the number of the Graf-follicles and of corpora lutea formed was compared. Occurrence of ovulation was detected by laparoscopy. The 100 μg D-Phe$^6$, Gln$^8$-GnRh analogue administered on the 7th day resulted in 15-36 ovulations after 41 hours in the infant pigs. Treatment of these animals produced similar results as described in Examples 1 to 3.

EXAMPLE 5

Inducing super-ovulation in infant sheep 10 50-day old female lambs were administered each intramuscularly twice daily for 5 days 10 μg doses each of D-Phe$^6$, Gln$^8$, desGly$^{10}$-GnRH ethylamide. The 70 μg active ingredient administered on the 6th day resulted in 3-9 ovulations in each of the animals. No change was observed in the animals used as control. Evaluation of treated and untreated control animals was carried out with the aid of laparoscopy. The results were similar to those outlined in Examples 1 to 4.

EXAMPLE 6

Inducing super-ovulation in infant cattle 8 65-old day infant calves were treated for 8 days, three times daily, with 2 μg of D-Phe$^6$, Gln$^8$, desGly$^{10}$-GnRH ethylamide each. After a day of rest, on the 10th day 100 μg active ingredient was administered each intramuscularly. Following the last injection, ovaries from both sides were removed; generally 5-11 developed Graf-follicles were registered in each ovary. 50% of the follicles were already past the stage when tight to the touch, i.e. they were follicles just prior to ovulation.

This test proves that even from infant animals several ripened ova could be obtained as opposed to the single ones in the adult animals, which number could be considered as physiological.

EXAMPLE 7

Treating physiological oligospermia of chimpanzee for achieving normospermia A fact, typical of animal species living in small groups, but specially of primates, often published in literature, that although all males in the group possess active libidos, only the dominant ones copulate, while subordinate males are physiologically and reversibly oligospermial. In our case, apart from sperm obtained from the dominant males, that was stored in sperm bank, we had to have expressly, for the purpose of insemination, sperm from the 4 subordinate males (all sexually mature). Before the treatment began, all animals were ejaculated under narcosis through electric shock method. Density and motility of the ejaculate was evaluated under microscope, then it was put under deep freeze probe ($-196°$ C.). In our previous spermatiological work we have found that defective sperms, that are hard to evaluate, do not survive deep freeze conditions. Favourable sperm picture after deep freeze indicated that spermiogenesis passed in order. Ejaculate of the males prior to treatment showed physiological oligospermia. Thereafter male chimpanzees weighing 60 to 90 kilograms were administered intramuscularly 100 μg of D-Phe$^6$, Gln$^8$, desGly$^{10}$-GnRH ethylamide diluted in 1 ml of normal saline solution using compressed air injection technique. 4 weeks after the first treatment and under narcosis ejaculate was obtained and 40-60% young sperm formations were registered, the ejaculates after deep freeze tests showed less than 10% motility. 60 days after the first treatment, the ejaculate obtained through electrical means under narcosis showed that the number of defective sperms fell below 30% and motility exceeded 60%. Qualitative and quantitative characteristics of the ejaculates were similar to those obtained from the dominant male and to values published in technical literature.

After diluting the ejaculate in a 1:1 ratio, deep-freeze test was positive and the 60% motility decreased to only 45%. Sperms of this quality either fresh or in deep freeze are entirely suitable for the purposes of insemination.

This process enabled us to obtain from subordinate males sperms in satisfactory quality and quantity that was storable in sperm bank and suitable for fertilization.

EXAMPLE 8

Inducing spermiogenesis of bison bull in seasonal oligospermia for collecting ejaculate suitable for insemination and deep freeze storage From bison bull belonging to Zoo and weighing 700 kg, under narcosis and by electrical means a sperm sample was obtained and it was established that it was in a seasonal oligospermial state. Symptoms of this were the following: under microscope magnifying 1500 times and used in sperm evaluation the number of sperm found was 5-20 and defective sperms reached 75-80%. The density of the ejaculate was 0.5. Sperms of this quality are unsuitable for fertilization.

Thereafter, twice weekly the animal was treated intramuscularly with 200-200 μg dose each of D-phe$^6$, Gln$^8$-GnRH analogue, using the compressed air injection method. On the 55th day following commencement of treatment, under narcosis and with a time lapse of one hour the animal was ejaculated twice. The two ejaculates were combined; their density was 4, their motility 55%. The thus-obtained sperms were deep frozen, then the decrease of motility as a result of deep freezing was checked: this was only 5%.

With this process we have succeeded in inducing the animal's spermiogenesis in such a way that instead of unsuitable sperms, ejaculate sperms of good quality were obtained which were suitable for inseminating females (14 animals) in fresh or deep-frozen condition.

EXAMPLE 9

Inducing spermiogenesis of red fox (*Vulpes vulpes*) in seasonal oligospermia

We have attempted to induce spermiogenesis of red fox males kept in Zoo and being in seasonal oligospermia with the aim that pure bred silver and blue foxes kept under farming scale conditions might be inseminated for the production of high-quality hybrid furs. In literature the fact is known that all sub-species of fox are only once in season every year, and apart from this gonads of both sexes are completely inactive. Between unoestrus of the various sub-species is a difference of several months (red fox: January; blue fox: April and May). Results of the test were compared to population being in seasonal unoestrus where the average quantity of ejaculate was 2 ml, density 3 and motility 50-60%. This was taken as physiological value.

During the test 5 sexually mature red fox males of 8 kg average weight were treated in the month of April, twice weekly with 1, 5, 10, and 50 $\mu$g doses of D-Phe$^6$, Gln$^8$-GnRH analogue for seven weeks. On the third week following commencement of treatment sperm sample was taken. In the sample sperm count was 70% of the physiological value, and the number of degenerated sperm was over 40%. Most of the deformed forms were of young formation (plasma droplet of neck and middle part). 7 weeks after the commencement of the test the animals were again ejaculated; from each animal sperms were successfully obtained in a volume from 1.2 ml to 3.1 ml, with a density of 3 and a motility of 65% which mathematically significantly exceeded the physiological value. (Males were separated from females, thus they had no opportunity to copulate.) Sperm samples were put into groups according to quality, then put into deep freeze. After dilution and deep freeze sperms stored at $-196°$ C. had a motility of 45% after remelting. Using deep-frozen sperms, successful pregnancy was achieved with blue foxes using GnRH ovulation programming (see Example 17) and insemination technique.

By ejaculating the 5 foxes once each, 56 doses of sperms suitable for fertilizing were obtained. In this way industrial technology service was provided for the production of quality furs.

EXAMPLE 10

Treating of Siberian tiger infertile owing to degenerated spermatogeny

A 8-year old Siberian tiger male of 120 kg and belonging to Zoo has lived with its mate for three years. Regular copulations took place on oestrus of the female, but no offspring was produced in any year. The possiblity that the female was at fault had to be excluded because previously she had pregnancy from an other male and the young ones born were reared as well. From the male in question through electrical means ejaculate was obtained under narcosis and it was established that it was very thin, 4-5 degenerate, vibrating sperms could be seen in each field of vision. Forms of degeneration were characteristic of the younger phases of spermiogenesis. Thereafter the animal was treated oncy weekly intramuscularly with a 100 $\mu$g dose of D-Phe$^6$, Trp$^7$, Leu$^8$-GnRH diluted in normal saline solution of 1 ml, using the compressed air injection technique. The male was kept with its mate and they copulated regularly during the treatments. The female became pregnant, producing three healthy offsprings.

Calculating from the time of birth, fertile copulation ensued 40-50 days following the first treatment.

Thus, the process of the invention is suitable for the treatment of degenerated spermatogeny in infertile male tiger and for the production of offsprings.

EXAMPLE 11

Stimulating physiological normospermia for obtaining hyperspermia suitable for deep freezing from Bengalian tiger A 8-year old Bengalian tiger of a weight of 200 kg belonging to Zoo copulated regularly, its mate becoming pregnant regularly for years. With this knowledge, under narcosis and in the mating season sperm sample was taken electrically and it was established that the sample density reached 3, motility was 30% and quantity of ejaculate amounted to 0.2 ml. Ejaculate showed a picture of physiological normospermia. Deep freezing of such minute quantity of ejaculate, however, is for technical reasons not possible. In order to protect the animal and to avoid liver damage, narcosis can be repeated every four days at the most and kept on for 4-5 hours. Collecting of sperms this way is unaccomplishable. In our process the male was separated from the female and was treated daily for 12 days with 10 $\mu$g each of D-Phe$^6$, Gln$^8$, DesGly$^{10}$-GnRH ethyl-amide which was diluted in 1 ml of normal saline solution and administered intramuscularly, using compressed air injection technique. On the 12th day, through electrical means the animal was ejaculated under narcosis twice with an hour time interval; in this way 1 ml and 0.8 ml of sperms were obtained. The two samples were combined and examined; a density of 4 was established, motility being 70%. Sperm samples were deep frozen and 21 doses suitable for artificial fertilization were prepared. Remelting sperms showed a motility of 60%.

With this process we have succeeded in obtaining from Bengalian tiger sperms of significant amount and storable in sperm bank.

EXAMPLE 12

Treating aspermia caused by non-natural keeping in orang-utan

A 18-year old, male orang-utan of a weight of ca. 350 kg and belonging to Zoo came into captivity in its infancy. Till the treatment it had three owners. Case history indicated that it has never a mate, was always alone and never copulated. It has been living in its present location for the past 11 years, it had neither a companion of his own kind nor a mate. He is phlegmatic, completely inactive, showing symptoms of hospitalization. The Zoo has been contacted that in case the animal is of Bornean Sub-species and fertile, it would be purchased. Chromosome test showed that the animal belongs to the extremely rare Bornean sub-species (altogether 153 exist in the whole world). A factor questioning fertility in the case-history was the absence of aggressiveness typical of the male primates and the ceasing of regular masturbation during hospitalization 5-6 years before. Sperm sample was taken from the animal under narcosis, using electrical means. In the ejaculate secretion of the side gonads was exclusively found, in three parts 1—1 droplet, altogether a quantity of 0.1 ml. Moving sperm in the ejaculate was not found and in the total ejaculate only a few inactive sperms could be observed (under microscope in 10 fields of vision only 1–2 were counted).

Thereafter the animal was treated twice weekly with a dose of 100 μg D-Phe$^6$, Gln$^8$, DesGly$^{10}$-GnRH ethylamide, i.e. similarly to the method used in Example 11. During treatment movement of the animal became more live and active. This, however, could not be attributed to the growth of libido, since it could have been caused by the fear from firing airgun injector. Treatment was finished on the 47th day following the first shot and ejaculate was taken twice under renewed narcosis and one hour interval; in this way altogether 3.2 ml of sperms were obtained. Density of sperm was 3, motility 35%. Amount of degenerated sperms reached 20%, practically made up of entirely young development forms (neck and middle part plasma droplets).

Because of the animal's extraordinarily high value and for the protection of personnel carrying out narcosis and ejaculation, treatment was stopped. The buyer was satisfied by the controlled sperm picture which was comparable to that characteristic of fertile primates.

With the above process we have corrected fertility of an extremely valuable rare animal and we succeeded in conserving its sperm that has become gene reserve appearing in international catalogues.

EXAMPLE 13

Ovarial inhibition of lion for purposes of contraception

In Zoos all over the world exhibiting the lion amongst big preditors is a common practice. In various panorama and safary allocation methods housing both sexes in the same living space, showing them together is a must. Of the preditors lion is the only one that in captivity under satisfactory feeding conditions breeds well. Due to saturation point of the "lion market" it is expedient to work out a process of contraception which is of no danger to the animal, will not cause changes in its appearance and behaviour, and prevents pregnancy despite of copulation. Sexual steroid-based contraception renders the animal unfit for exhibition within a short time (abnormal adiposity).

In our process an intact, fertile female lion belonging to a Zoo was treated, a lioness of 200 kg body weight, which has given litter five times in its life already. Treatments took place twice in every 3 weeks, using D-Phe$^6$, Gln$^8$-GnRH analogue. Treatment was timed in such a way that a 50 μg dose was follwed by a 500 μg dose, than a 3-week pause followed. Treatment was carried out with the already mentioned three weeks interval from commencement of oestrus (month of April) until 50 days following end of oestrus typical of the species (August). The animal exhibited normal behaviour, copulated regularly in oestrus, its mate being normospermial after examination. During treatment the animal did not become pregnant, showed no irregularity either in its behaviour or in its appearance.

EXAMPLE 14

Inducing rutting of female piglets in puberty kept under industrial farming conditions for inducing "first successful rutting"

Under industrial farming conditions sows allocated for breeding to replace stocks have to be bred as early as possible as well as fertilized and farrowed in a synchronised way that fits into the industrial farming technology. Gonad activity of female animals in prepuberty and puberty due to their being in large herds, fed intensively and ferced to grow fast, is unstable and, for this reason, fertile ruttings occur rarely, appearing scattered in the stock.

For our tests 60 potential breeding sows were selected from a stock of 200 sows available at the farm, on the basis of best growing vigor and feed conversion determined by industrial technology. These animals were put into 2 random groups of 30 each. Both groups, also according to industrial technology, were kept without food and drink for 24 hours. Animals at time of selection were injected intramuscularly with D-Phe$^6$, Gln$^8$-GnRH analogue diluted in normal saline solution, then injections were repeated with 20 μg doses each from the same analogue twice with 24 hours intervals. The first rutting animal appeared 5 days after selection both in the untreated control group and in the treated group. Both groups were kept in the same sty, air-space, under similar conditions for 26 days as permitted in the industrial farming technology. During this time 3 animals (10%) from the untreated control and 21 animals (70%) from the treated stock rutted successfully. Only those ruttings were considered succesful which resulted in normal births.

In this test series exact timing of ovulation was not amongst aims since only a few boars were available. For this reason, aim of the treatment was "the first successful rutting" within 26 days. 10% of the sows in farrow was a result acceptable to industrial farming average, thus the increase to 70% as a result of treatment means a very significant economic advantage.

EXAMPLE 15

Treatment of chinchilla being barren for prolonged time

Twenty chinchillas barren for at least two years were treated twice daily for three days with 10 μg each of D-Phe$^6$, Gln$^8$-GnRH analogue through intraperitoneal injection. On the 4th day the animals were injected with 75 μg of GnRH analogue, then they were put together with the male. 12 of the Chinchillas gave birth within 4 months.

Parallel with the above treatment, 3 animals barren for more than 2 years having very valuable fur as "black" mutant chinchillas were treated twice daily for three days with 10 μg each of D-Phe$^6$, Gln$^8$-GnRH analogue, administered through peritoneal injection. The animals were injected on the 4th day with 75 μg of GnRH analogue, then, as customary, were put together with the male. Within four months all three animals gave birth to young ones.

With this process we have succeeded in bringing into renewed production barren animals of prolonged time with valuable fur.

EXAMPLE 16

Cancelling seasonal unoestrus in adult wild cat (*Felis silvestris*)

2 female wild cats from Zoo, with an average weight of 6 kg and having under normal conditions a cycle between February and March, were treated with D-Phe$^6$, Gln$^8$, desGly$^{10}$-GnRH ethyl-amide. Before treatments began, abdominal cavity was opened under narcosis in order to see the condition of both ovaries. After sewing up the abdomen, animals were treated every second day, four times in total through intramuscular injection of the active ingredient diluted in normal saline solution. A two-hour interal was kept between the first and second injection; the first dose was 100 μg, the second one 500 μg. This was followed after 48 hours by the third dose of 100 μg, then two hours later by the fourth dose of 500 μg. On the 0., 2., 4. and 8th day of the treatment abdomen was opened under narcosis and changes in condition of the ovaries were visually evaluated. After treatment both ovaries were removed, fixed and their hystological evaluation was carried out.

On the 0. day of the treatment on left side ovary of both animals 3–4 supposed secondary follicles and 1 degenerated old corpus luteum, while on the right side ovary 5–6 supposed secondary follicles could be seen. As a result of treatment, after 4 days all secondary follicles turned into Graf-follicles ovulated, and in their places corpora haemorrhgica turning into corpora lutea were found. Alongside corpora haemorrhagica visually not countable secondary follicles developed, which, as a result of the next treatments, developed further and, as a result of the last 500 μg dose, they atretized with intrafollicular luteinisation. Hystological evaluation gave complete support to visual findings.

Ovulation resulting from the above treatment proves that in the case of felines fertilization out of season can be achieved and even in unnatural keeping offsprings can be produced.

EXAMPLE 17

Treatment of female blue fox in seasonal unoestrus for inducing fertile oestrus

Female blue fox in seasonal unoestrus was examined in December under narcosis with the aid of laparoscopy. It was determined that ovaries on both sides were inactive, and growing of Graf-follicles could not be seen on them.

Then the animal had twice daily intramuscular treatment for ten days with a 1 to 5 μg dose of D-Phe$^6$, Gln$^8$-GnRH analogue. On the tenth day another laparoscopy was carried out under narcosis. It was found that on ovaries of both sides there were large corpora lutea but, due to imperfect technique, their number could only be estimated to be about 10 to 20. At the same time it was established that the neck of uterus was open.

Also in December a rejected female due to mammalian atrophy was similarly treated twice a day with 2 μg each of D-Phe$^6$, Gln$^8$-GnRH analogue the effect of which was followed by looking at changes in condition of the neck of uterus. On the 6th day following first treatment, the neck of uterus opened. At this time the treatment was carried out with 50 μg of active ingredient. 16 hours later conditions of the ovaries were examined with mirroring and a state immediately prior to ovulation was found. Then abdominal cavity was entirely opened, the ovaries were removed and by puncturing ova were removed from a total of 11 Graf-follicles. Six regular, normal ova covered with corona radiata were found.

With the above process we made possible production of in vitro fertilizable ova and also embryos in seasonal anoestrus and not disturbing normal heat.

In this way the producing of specially valuable hybrids is made possible with the use of less valuable recipient animals.

EXAMPLE 18

Stimulating function of ovary in infant domestic cat (*Felis cattus domesticus*) with the aid of D-Phe$^6$, Gln$^8$-GnRH analogue 5 kittens each weighing 0.3 kg and being 45 days old were treated with D-Phe$^6$, Gln$^8$-GnRH analogue every second day, altogether 4 times, using 100 μg each of the active ingredient. It was intramuscularly administered after dilution in normal saline solution. Following treatment, ovaries of both sides were removed from the animals under narcosis and visual examination took place. Thereafter the ovaries were fixed in formalin, and then hystological test was carried out. It was found that there were 5–7 corpora haemorrhagica on ovaries of both sides. Under incrustation developing follicles were found, well definable from the bright, butter-coloured ovary. Some of the follicles were of Graf-follicle size. Animals not treated with active ingredient did not show this change.

These results unambiguously prove that ovary of infant domestic cat as a result of the above treatment will show characteristics of sexually mature animals on hystological and morphological examination. Thus the animal becomes suitable for production of ova ready for in vitro fertilization before traditional sexual maturity.

EXAMPLE 19

Stimulating function of ovary in domestic cat with D-Phe$^6$, Trp$^7$, Leu$^8$-GnRH analogue 5 kittens each weighing 0.3 kg and being 45 days old were treated with D-Phe$^6$, Trp$^7$, Leu$^8$-GnRH analogue in such a way that prior to treatments the left side ovary was removed under narcosis. Then the mediums were treated every second day, three times in all with doses of 100 μg each of the active ingredient diluted in normal saline solution administered intramuscularly. After treatment the remaining right side ovaries were removed, examined visually, then, after fixing, hystological examination was carried out.

Ovaries removed prior to treatment were quite homogeneous, butter-yellow in colour, growing follicle could not be detected in them either visually or hystologically. Following treatment 7–8 corpora haemorrhagica and several (not countable) growing follicles were found.

Result of the trial even with the use of a different active analogue ingredient gave support to results as described in Example 18 and gave further evidence of the fact that subsequent cycle of the ovary develops physiologically.

EXAMPLE 20

Stimulating pri-mordial follicles in infant domestic female cat (*Felis cattus domesticus*)

5 kittens of 0.3 kg weight and being 45 days old were treated with D-Phe$^6$, Gln$^8$-GnRH analogue in such a way that under narcosis the left-side ovary was removed. Thereafter the medium was treated for three days, three times daily, with a 4-hour time interval between treatments. Treatment was carried out nine times in all and every instance a 0.1 μg dose of the analogue was used. The active ingredient was suspended in normal saline solution and propyleneglycol and it was administered intramuscularly. After treatment remaining ovaries were removed, evaluated visually, then after fixing hystological examination was performed. Visually both ovaries were butter-yellow, looked homogeneous, but the treated ovary was slightly enlarged. In the untreated ovaries only premordial follicles were found and could be evaluated hystologically, while on the section side of the treated ovary non-countable (many hundreds of) follicles were found which started to grow and were in various stages of anthrum formation.

With the above process we have succeeded in simultaneously stimulating many hundreds of primordial follicles in the ovary.

EXAMPLE 21

Production of ova in cattle for embryo rearing in vitro from organ culture

Cattle in slaughter-house was stunned and bled, after which intact ovaries were removed within 30–55 minutes. Then in laboratory conditions they were placed in complete adjuvant. To this culture liquid D-Phe$^6$, Gln$^8$, desGly$^{10}$-GnRH ethyl-amide was given in a concentration of $10^{-9}$–$10^{-8}$ g/ml. Ovary stock took 16 to 43 hours to ovulate in organ culture. Out of the spontaneous ovulations of in vitro ovaries and from ova obtained with puncturing 85% were capable to continue meiosis (reductive cell division) and to be successfully fertilized in vitro by tractable sperms of cattle. First two divisions of cells was observed in the culture amongst in vitro fertilized ova.

With this process we have created an opportunity that, similarly to insemination technology used with cattle world over, renders possible live embryos to be "inseminated" and transplanted, respectively. In slaughter-houses there is a possibility of producing embryos with the above process far in excess to the requirement of industry.

We claim:

1. A process for producing sexual products suitable for natural or artificial fertilization from the sex organs of mammals during prenatal life, postnatal life, infancy, puberty or the mature state, to produce offspring therefrom and to increase several times the production of sexual products to a level far above that typical of the species comprising treating a mammal at least once and at most 60 times with a gonadotropin-releasing hormone analogue selected from the group consisting of Glp-His-Trp-Ser-Tyr-D-Phe-Trp-Leu-Pro-Gly-NH$_2$ Glp His-Trp-Ser-Tyr-D-Phe-Leu-Gln-Pro-Gly-NH$_2$ Glp-His-Trp-Ser-Tyr-D-Phe-Leu-Gln-Pro-NHCH$_2$CH$_3$ or a salt or metal complex thereof in a dose of 0.01 to 500 μg/kg body weight wherein an interval of at least two hours and at most 7 days is kept between individual treatments.

2. The process of claim 1 wherein the gonadotropin-releasing hormone analogue is Glp-His-Trp-Ser-Tyr-D-Phe-Trp-Leu-Pro-Gly-NH$_2$.

3. The process of claim 1 wherein the gonadotropin-releasing hormone analogue is Glp-His-Trp-Ser-Tyr-D-Phe-Leu-Gln-Pro-Gly-NH$_2$.

4. The process of claim 1 wherein the gonadotropin-releasing hormone analogue is Glp-His-Trp-Ser-Tyr-D-Phe-Leu-Gln-Pro-NHCH$_2$CH$_3$.

5. The process of claim 1 wherein the mammal is treated one to five times with said gonadotropic-releasing hormone analogue.

6. The process of claim 1 wherein the dose of said gonadotropin-releasing hormone analogue is 1 to 100 μg/kg body weight.

7. The process of claim 1 wherein the interval between treatments is 2 to 8 hours.

8. The process of claim 1 wherein the mammal is treated one to five times with said gonadotropin-releasing hormone at a dose of 1 to 100 μg/kg body weight at an interval of 2 to 8 hours between treatments.

9. The process of claim 1 wherein the gonadotropin-releasing hormone analogue used to treat the mammal is incorporated with a veterinary carrier or excipient.

* * * * *